United States Patent [19]

Nishino

[11] Patent Number: 5,311,284
[45] Date of Patent: May 10, 1994

[54] METHOD OF MEASURING OPTICAL CHARACTERISTICS OF THIN FILM AND APPARATUS THEREFOR

[75] Inventor: Toshiharu Nishino, Hamura, Japan

[73] Assignee: Casio Computer Co., Ltd., Tokyo, Japan

[21] Appl. No.: 909,630

[22] Filed: Jul. 7, 1992

[30] Foreign Application Priority Data

Jul. 12, 1991 [JP] Japan ................... 3-172610

[51] Int. Cl.$^5$ ............... G01J 4/00; G01B 11/06
[52] U.S. Cl. .................... 356/364; 356/365; 356/366; 356/367; 356/368; 356/382
[58] Field of Search ............ 356/364, 365, 366, 367, 356/368, 382

[56] References Cited

U.S. PATENT DOCUMENTS

| | | | |
|---|---|---|---|
| 3,158,675 | 11/1964 | Murray et al. ............ | 356/367 |
| 3,941,482 | 3/1976 | Schneider ............... | 356/365 |
| 3,985,447 | 10/1976 | Aspnes .................. | 356/382 X |
| 4,801,798 | 1/1989 | Lange ................... | 356/367 X |
| 4,873,430 | 10/1989 | Juliana et al. .......... | 356/382 |
| 4,878,755 | 11/1989 | Siegmund et al. ......... | 356/382 |
| 4,973,163 | 11/1990 | Sakai et al. ............ | 356/367 |
| 4,999,014 | 3/1991 | Gold et al. ............. | 356/382 |
| 5,101,111 | 3/1992 | Kondo ................... | 356/382 X |

OTHER PUBLICATIONS

The Review of Scientific Instruments, vol. 40, No. 6, Jun. 1969, pp. 761–727. An Improved Method for High Reflectivity Ellipsometry Based on a New Polization Modulation Technique.
Applied Optics, vol. 14, No. 3, Mar. 1975, pp. 757–760, High Frequency Polarization Modulation Method for Measuring Birefringence.

*Primary Examiner*—James C. Housel
*Assistant Examiner*—Milton I. Cano
*Attorney, Agent, or Firm*—Frishauf, Holtz, Goodman & Woodward

[57] ABSTRACT

In a first step, the value of the synthetic retardation and the direction of the synthetic optical axis as angle data of a transparent substrate having a thin film thereon are measured. In a second step, the value of the retardation and the direction of an optical axis as angle data of only the transparent substrate are measured. In a third step, the value of the retardation and the direction of an optical axis as an angle of only the thin film are calculated in accordance with the following equations on the basis of the value of the retardation and the angle data of the direction of the optical axis which are calculated in the first step and the value of the retardation and the angle data of the direction of the optical axis of only the transparent substrate which are calculated in the second step:

$$\Delta_1 = \{\Delta_{12}^2 + \Delta_2^2 - 2\Delta_{12}\Delta_2 \cos 2(\theta_{12} - \theta_2)\}^{\frac{1}{2}}$$

$$\theta_1 = \tfrac{1}{2} \tan^{-1}\left(\frac{\Delta_{12} \sin 2\theta_{12} - \Delta_2 \sin 2\theta_2}{\Delta_{12} \cos 2\theta_{12} - \Delta_2 \cos 2\theta_2}\right).$$

17 Claims, 3 Drawing Sheets

METHOD OF MEASURING OPTICAL CHARACTERISTICS OF THIN FILM AND APPARATUS THEREFOR

BACKGROUND OF THE INVENTION

1. Field of the Invention

The present invention relates to a method of measuring optical characteristics such as the retardation and the direction of an optical axis of a thin film formed on a transparent substrate, and an apparatus therefor.

2. Description of the Related Art

Measurement of optical characteristics of an optically anisotropic thin film such as an alignment film formed on a substrate surface of a liquid crystal display device or the like is generally performed by the following method. A target thin film to be measured is formed on a transparent substrate such as a glass substrate, light is radiated from a laser onto this substrate having the thin film thereon through a polarizer and a photoelastic modulator, light passing through the substrate and the target film is detected by a photodetector through an analyzer, and optical characteristics of the target thin film, i.e., the retardation (the difference between the lengths of optical paths of ordinary and extraordinary rays) and an angle θ of an optical axis (phase-delay or phase-advance axis) in accordance with arithmetic operations.

In the above conventional method of measuring the optical characteristics, however, since light detected by the analyzer is light having passed through the target thin film and the substrate having this thin film thereon, the retardation and the angle of the optical axis of the target thin film cannot be accurately measured, resulting in inconvenience.

This inaccuracy in measurement is caused since the substrate having the target thin film thereon also has optical anisotropy and, for this reason, the measured retardation and the measured angle of the optical axis represent the synthetic optical characteristics of both the target thin film and the substrate.

SUMMARY OF THE INVENTION

It is an object of the present invention to provide a method of measuring optical characteristics of a thin film so as to accurately measure the retardation and the angle of an optical axis of the thin film formed on a transparent substrate.

In order to achieve the above object according to the present invention, there is provided a method of measuring optical characteristics, comprising:

the synthetic retardation measuring step of measuring a value of a synthetic retardation and a direction of a synthetic optical axis of a transparent substrate and a thin film on the basis of a polarized state of light passing through the transparent substrate and the thin film formed thereon;

the substrate retardation measuring step of measuring a value of a retardation and a direction of an optical axis of only the transparent substrate on the basis of a polarized state of light passing through only the transparent substrate on which the thin film is not formed; and the retardation arithmetic operation step for calculating a value of a retardation and a direction of an optical axis of only the thin film on the basis of the value of the synthetic retardation and the direction of the synthetic optical axis which are measured in the synthetic retardation measuring step and the value of the retardation and the direction of the optical axis of only the transparent substrate, which are measured in the substrate retardation measuring step.

According to the method of measuring the optical characteristics of the present invention, the synthetic retardation and the direction of the synthetic optical axis of the transparent substrate and the target thin film are measured independently of the retardation and the direction of the optical axis of only the transparent substrate. The optical characteristics of the target thin film are calculated on the basis of these measured data. Therefore, the resultant values of the optical characteristics of the target thin film are not adversely affected by the optical characteristics of the transparent substrate, and the characteristics of only the thin film can be accurately and easily measured while the target thin film is kept formed on the transparent substrate.

According to the present invention, there is also provided an apparatus for measuring optical characteristics, comprising:

means for measuring a retardation and a direction of an optical axis of only a transparent substrate and a synthetic retardation and a direction of a synthetic optical axis of the transparent substrate having a thin film thereon in a predetermined order;

means for holding one of first data consisting of the retardation and the direction of the optical axis of only the transparent substrate, which are measured by the measuring means, and second data consisting of the synthetic retardation and the direction of the synthetic optical axis of the transparent substrate having the thin film thereon; and retardation arithmetic operation means for calculating a value of a retardation and a direction of an optical axis of only the thin film on the basis of the other data from the measuring means and one data from the holding means.

The apparatus for measuring the optical characteristics of the present invention includes the means for holding the data measured by the means for measuring the retardation and the direction of the optical axis and the means for calculating the data holded in the holding means and the data from the measuring means. Therefore, the characteristics of only the thin film can be accurately and easily measured while the target thin film is kept formed on the transparent substrate.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENT

An embodiment of the present invention will be described with reference to the accompanying drawings.

An apparatus for measuring optical characteristics according to the embodiment of the present invention comprises an optical system for radiating light on a target thin film 10 to be measured and detecting light passing through the target thin film 10, an arithmetic operation unit 30 for performing arithmetic operations on the basis of data detected by the optical system, and a control unit 8 for controlling the optical system and the arithmetic operation unit 30.

Figure 1:
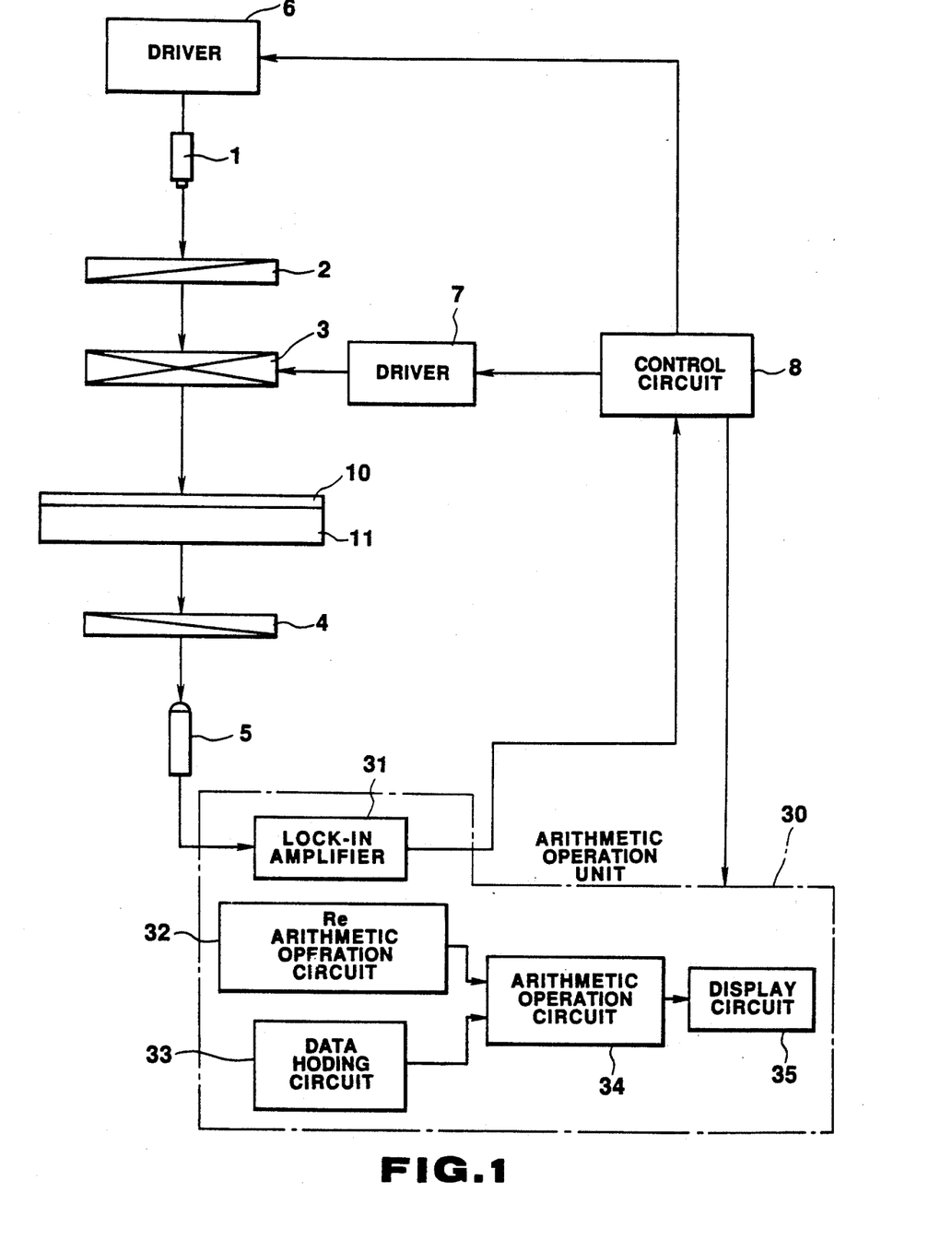
FIG. 1 is a schematic diagram showing an apparatus for measuring optical characteristics according to the present invention.
Figure 2:
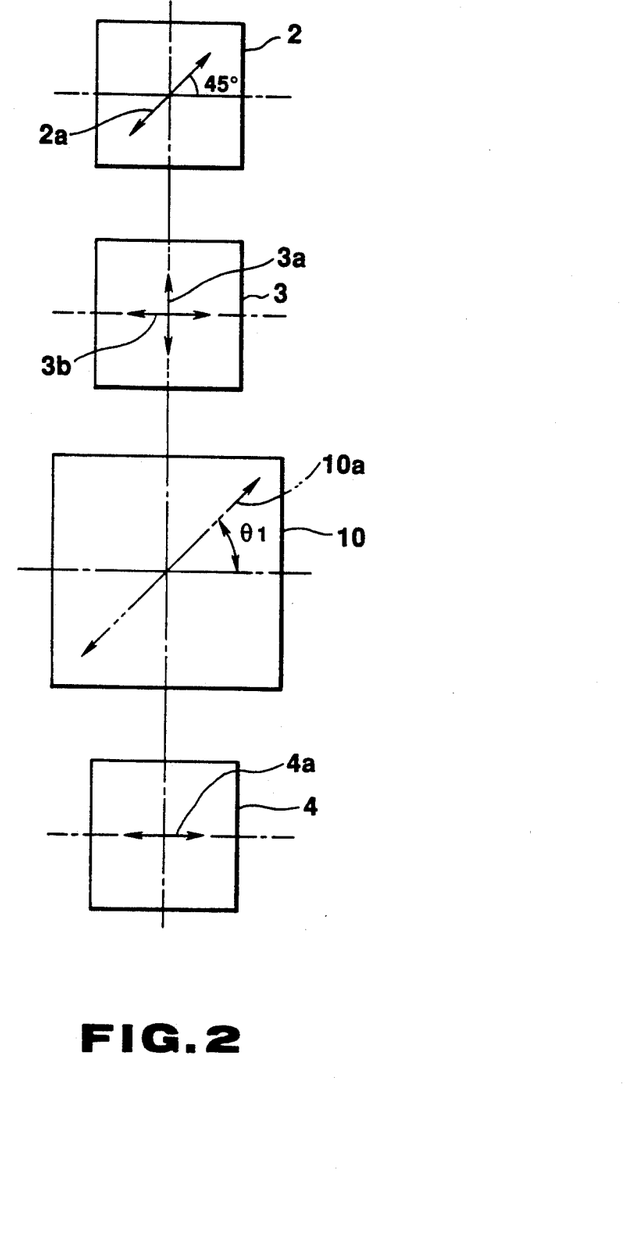
FIG. 2 is a schematic plan view showing the layout of optical axes of optical members in the apparatus measuring the optical characteristics of the present invention.

The optical system comprises a polarizer 2, a photoelastic modulator 3, a substrate 11 having the target thin film 10 thereon, and an analyzer 4, all of which are arranged on a linear optical path passing through a laser oscillator 1 and a photodetector 5. Optical axes 2a, 3a, 3b, and 4a of the optical members 2, 3, and 4 are set, as shown in FIG. 2. More specifically, the transmission axis 2a of the polarizer 2 is inclined at 45° with respect to the two orthogonal optical axes 3a and 3b of the photoelastic modulator 3, and the transmission axis 4a of the analyzer 4 is inclined at 45° with respect to the transmission axis 2a of the polarizer 2. The target thin film 10 is located between the photoelectric modulator 3 and the analyzer 4.

The photoelastic modulator 3 is arranged to cause an elastic strain in a crystal and change the refractive index in a predetermined direction. The photoelastic modulator 3 is an optical element for oscillating a difference in refractive index between ordinary light and extraordinary light in accordance with a signal having a predetermined frequency $\omega$ supplied from a driver 6.

The laser oscillator 1 is connected to a laser oscillator driver 6, and the photoelastic modulator 3 is connected to a photoelastic modulator driver 7. The drivers 6 and 7 are driven in accordance with control signals from a control circuit 8 for controlling the drivers 6 and 7. A pulsed laser beam synchronized with the frequency $\omega$ is generated by the laser oscillator 1 and is radiated on the photoelastic modulator 3. The laser beam which is modulated by the photoelastic modulator 3 and the polarized state of which is changed by the frequency $\omega$ is radiated on the target thin film 10 and the substrate 11.

The laser beam passing through the target thin film 10 and the substrate 11 is incident on the photodetector 5 through the analyzer 4 and is converted into a light intensity signal by the photodetector 5. The converted signal is input to a lock-in amplifier 31. This lock-in amplifier 31 extracts a signal having the predetermined frequency component ($\omega$ component) from the light intensity signal from the photodetector 5. The extracted signal is supplied to a retardation arithmetic operation circuit 32. The signal having the predetermined frequency $\omega$ is supplied to the control circuit 8.

The retardation arithmetic operation circuit 32 connected to the lock-in amplifier 31 calculates, as optical characteristic data, the value of the retardation and the direction of an optical axis as angle data $\theta_1$ of the target thin film 10 and the substrate 11 on the basis of an output signal from the lock-in amplifier 31.

The calculated optical characteristic data are supplied to a data holding circuit 33 and an arithmetic operation circuit 34. The arithmetic operation circuit 34 performs an arithmetic operation on the basis of the optical characteristic data from the retardation arithmetic operation circuit 32 and the optical characteristic data from the data holding circuit 33 in accordance with an algorithm to be described later. The calculated optical characteristic data are display on a displayed unit 35 or a display circuit.

In order to measure the value of the retardation and the angle $\theta_1$ of the optical axis of the target thin film 10 using the above apparatus for measuring the optical characteristics, the substrate 11 having the target thin film 10 is placed between the photoelastic modulator 3 and the analyzer 4.

This target thin film 10 is an alignment film used in a liquid crystal display unit. This alignment film is formed by depositing on the substrate 11 a monomolecular film in which single molecules are aligned in one direction by an LB method, or coating an aligning material such as polyimide on the substrate 11 and rubbing the surface of the alignment material film. This alignment film has optical anisotropy.

Measurement of optical characteristics (i.e., the retardation and an angle $\theta_1$ of an optical axis) of the target thin film 10 is performed by the following method. Polarized light is radiated on the target thin film 10 formed on the substrate 11 to measure a retardation and an angle (i.e., an angle with respect to the x- or y-axis) which are obtained as synthesized optical characteristics of both the target thin film 10 and the substrate 11 from the intensity of light passing through both the thin film 10 and the substrate 11. At the same time, polarized light is radiated on the substrate 11 without forming the target thin film 10 thereon to measure the retardation and the angle of the optical axis of only the substrate 11 from the intensity of light transmitted through the substrate 11. The retardation and the angle of the optical axis of only the target thin film 10 are calculated in accordance with the synthesized retardation (to be referred to a synthetic retardation hereinafter) and the angle of the synthesized optical axis (to be referred to as a synthetic optical axis hereinafter) and the retardation and the angle of the optical axis of only the substrate 11.

The measurement of the synthetic retardation and the angle of the synthetic optical axis will be described below. Output light from the laser oscillator 1 is converted into linearly polarized light through the polarizer 2. The linearly polarized light is incident on the upper surface of the target thin film 10 through the photoelastic modulator 3.

The light passing through the photoelastic modulator 3 is light whose polarized state is modulated in accordance with a modulation frequency $\omega$ of the photoelastic modulator 3. The polarized state of the modulated light is changed between the linearly polarized light and elliptically polarized light.

When the modulated light is incident on the target thin film 10, the polarized state of this light is changed through the thin film 10 in accordance with the optical anisotropy of the thin film 10. Therefore, the modulated light becomes light having a polarized state in which a phase difference caused by the anisotropy of the thin film is superposed on a phase difference between ordinary light and extraordinary light.

The light passing through the target thin film 10 passes through the substrate 11 and emerges from the lower surface of the substrate 11. At this time, when the substrate 11 has optical anisotropy, the polarized state of the light having passed through the target thin film 10 is further changed in accordance with the optical anisotropy of the substrate 11 during optical transmission through the substrate 11.

The light emerging from the lower surface of the substrate 11 is incident on the analyzer 4. A light component on the transmission axis from the analyzer 4 is incident on the photodetector 5, and the photodetector 5 detects the intensity of the incident light. The analyzer 4 outputs a signal corresponding to the detected light intensity to the lock-in amplifier 31.

The light intensity detected by the photodetector 5 is a value corresponding to the synthetic retardation caused by the optical anisotropies of the target thin film 10 and the substrate 11. This value is superposed on the modulation frequency $\omega$.

The lock-in amplifier extracts a frequency component of the modulation frequency $\omega$ from the light-intensity signal received from the photodetector 5 and calculates the synthetic retardation and the angle of the synthetic optical axis of the optical elements (the target thin film 10 and the substrate 11 in FIG. 1) located between the photoelastic modulator 3 and the analyzer 4 on the basis of the light intensity of this frequency component in accordance with a known arithmetic operation technique.

The calculated retardation and the calculated angle of the synthetic optical axis are those of the target thin film 10 and the substrate 11 since the optical elements are the target thin film 10 and the substrate 11 (located between the photoelastic modulator 3 and the analyzer 4). That is, the calculated values represent the synthetic retardation and the angle of the synthetic optical axis of the target thin film 10 and the substrate 11. The calculated synthetic retardation and the calculated angle data of the synthetic optical axis are stored in the holding circuit 33.

After the synthetic retardation and the angle of the synthetic optical axis are measured, the retardation and the angle of the optical axis of the substrate 11 are measured by removing the target thin film 10 from the substrate 11 or using a substrate identical to the substrate 11 having the thin film 11 thereon such that the substrate 11 without the target thin film 10 is located between the photoelastic modulator 3 and the analyzer 4 in the same manner as in measurement of the synthetic retardation and the angle of the synthetic optical axis.

In this case, since the optical element located between the photoelastic modulator 3 and the analyzer 4 is only the substrate 11, the retardation and the angle of the synthetic optical axis which are calculated by the above arithmetic operation unit are those of only the substrate 11.

Note that the target thin film 10 on the substrate 11 is removed by, e.g., dry etching. In this case, since the substrate 11 consists of an inorganic material such as glass and the thin film 10 consists of an organic material such as an alignment film, only the thin film 10 can be removed without adversely affecting the substrate 11.

The retardation and the angle of the optical axis of the target thin film 10 are calculated by the arithmetic operation circuit 34 such that the retardation and the angle of the optical axis of only the substrate 11 which are derived from the retardation arithmetic operation circuit are subtracted from the synthetic retardation and the angle of the synthetic optical axis of the target thin film 10 and the substrate 11 which are similarly measured and stored in the holding circuit.

The arithmetic operation for calculating the retardation and the angle of the optical axis of the target thin film 10 are derived from a Jones matrix as follows.

Figure 3:
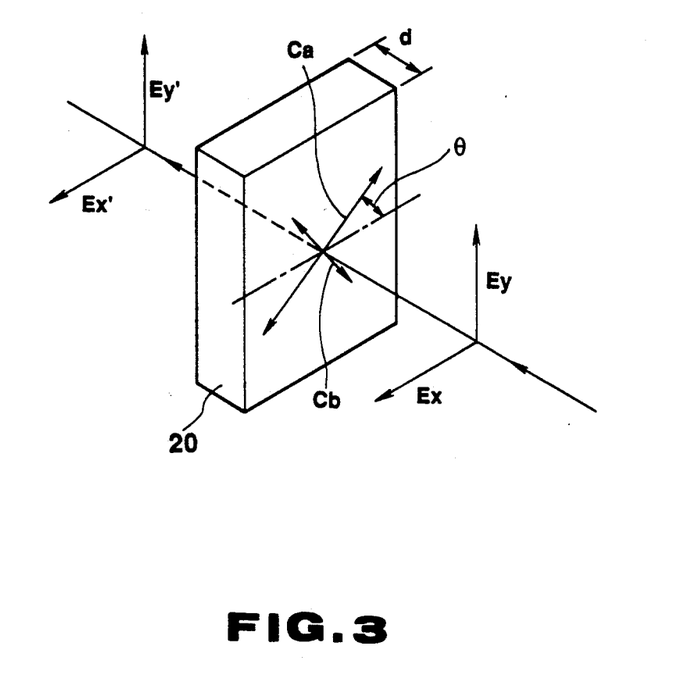
FIG. 3 is a perspective view showing electrical vectors of light passing through an optical medium.

The Jones matrix will be described below. FIG. 3 is a view showing electrical vectors of light passing through an arbitrary optical element 20 having optical anisotropy. Reference symbol Ex denotes an x component of an electrical vector of incident light; Ey, a y component of the electrical vector of the incident light; Ex', an x component of an electrical vector of exit light; and Ey', a y component of the electrical vector of the exit light.

A relationship between the electrical vector of the incident light on the optical element 20 and the electrical vector of exit light emerging from the optical element 20 is given by equation (3-1). In equation (3-1), A represents the Jones matrix of the optical element 20, and a value obtained by multiplying the electrical vector of the incident light with the Jones matrix A is given as the electrical vector of the exit light. The electrical vector of the incident light is defined by equation (3-2), and the Jones matrix A of the optical element 20 is represented by equation (3-3):

$$\vec{E'} = A \cdot \vec{E} \tag{3-1}$$

$$\vec{E} = \begin{bmatrix} Ex \\ Ey \end{bmatrix} \tag{3-2}$$

$$A = \begin{bmatrix} a & b \\ c & d \end{bmatrix} \tag{3-3}$$

where
$\vec{E}$: the electrical vector of the incident light
$\vec{E'}$: the electrical vector of the exit light
Ex: the x component of the electrical vector
Ey: the y component of the electrical vector
A: the Jones matrix On the other hand, the retardation $\Delta$ of the optical element 20 is represented by the product of a birefringence $\delta n$ of the optical element 20 and a thickness d of the optical element 20 in the light-transmitting direction, i.e., $\Delta = \delta n \cdot d$. Note that the birefringence $\delta n$ is represented by the difference ($\delta n = n_a - n_b$) between a refractive index $n_a$ of the optical element 20 in a phase-delay axis $C_a$ and a refractive index $n_b$ of the optical element 20 in a phase-advance axis $C_b$.

When the phase-delay axis $C_a$ and the phase-advance axis $C_b$ of the optical element 20 having the above optical anisotropy are directed, as shown in FIG. 2, and the angle of one of these optical axes, e.g., the phase-delay axis $C_a$ with respect to the reference line (the x axis in this embodiment) is defined as $\theta$ (the phase-delay axis $C_a$ and the phase advance axis $C_b$ are orthogonal), the Jones matrix of the optical element 20 is represented by the following matrix (4-1). When this matrix (4-1) is developed and rewritten, matrix (4-2) is obtained. When the value of the retardation $\Delta$ of the optical element 20 is assumed to be a sufficiently small value, and matrix (4-2) is rewritten using an approximate value, matrix (4-3) is derived as follows.

$$\begin{bmatrix} \cos\theta & -\sin\theta \\ \sin\theta & \cos\theta \end{bmatrix} \begin{bmatrix} e^{-i\Delta/2} & 0 \\ 0 & e^{i\Delta/2} \end{bmatrix} \begin{bmatrix} \cos\theta & \sin\theta \\ -\sin\theta & \cos\theta \end{bmatrix} \quad (4\text{-}1)$$

$$\begin{bmatrix} e^{-i\Delta/2}\cos^2\theta + e^{i\Delta/2}\sin^2\theta & -(e^{i\Delta/2} - e^{-i\Delta/2})\sin\theta\cos\theta \\ -(e^{i\Delta/2} - e^{-i\Delta/2})\cos\theta\sin\theta & e^{i\Delta/2}\cos^2\theta + e^{-i\Delta/2}\sin^2\theta \end{bmatrix} \quad (4\text{-}2)$$

wherein if $\Delta << 1$, then $e^{\pm i\Delta/2} = 1 \pm i\Delta/2$, so that matrix (4-2) can be rewritten as follows:

$$\begin{bmatrix} 1 - i\frac{\Delta}{2}\cos2\theta & -i\frac{\Delta}{2}\sin2\theta \\ -i\frac{\Delta}{2}\sin2\theta & 1 + i\frac{\Delta}{2}\cos\theta \end{bmatrix} \quad (4\text{-}3)$$

Assuming that the optical element 20 is substituted with the target thin film 10, let $\Delta_1$ be the retardation of the thin film 10, and $\theta_1$ be the angle of one optical axis (e.g., the phase-delay axis) with respect to the reference line. Under these assumptions, the Jones matrix of the target thin film 10 is represented by the following matrix (5):

$$\begin{bmatrix} 1 - i\frac{\Delta_1}{2}\cos2\theta_1 & -i\frac{\Delta_1}{2}\sin2\theta_1 \\ -i\frac{\Delta_1}{2}\sin2\theta_1 & 1 + i\frac{\Delta_1}{2}\cos2\theta_1 \end{bmatrix} \quad (5)$$

Similarly, let $\Delta_2$ be the retardation of the substrate 11, and $\theta_2$ be the angle of one optical axis (e.g., the phase-delay axis) with respect to the reference line. Under these assumptions, the Jones matrix of the substrate 11 is represented by the following matrix (6):

$$\begin{bmatrix} 1 - i\frac{\Delta_2}{2}\cos2\theta_2 & -i\frac{\Delta_2}{2}\sin2\theta_2 \\ -i\frac{\Delta_2}{2}\sin2\theta_2 & 1 + i\frac{\Delta_2}{2}\cos2\theta_2 \end{bmatrix} \quad (6)$$

Assuming that the substrate 11 having the target thin film 10 thereon is regarded as a single optical element, let $\Delta_{12}$ be the retardation of the optical element consisting of the substrate 11 and the thin film 10, and $\theta_{12}$ be the angle of the optical axis of the optical element. Under these assumptions, the Jones matrix of this optical element is represented by matrix (7) as follows:

$$\begin{bmatrix} 1 - i\frac{\Delta_{12}}{2}\cos2\theta_{12} & -i\frac{\Delta_{12}}{2}\sin2\theta_{12} \\ -i\frac{\Delta_{12}}{2}\sin2\theta_{12} & 1 + i\frac{\Delta_{12}}{2}\cos2\theta_{12} \end{bmatrix} \quad (7)$$

In measurement of the optical characteristics of the target thin film 10 formed on the substrate 11, values to be actually measured are the synthetic retardation $\Delta_{12}$ and an angle $\theta_{12}$ of the synthetic optical axis, which are obtained by synthesizing the optical characteristics of both the target thin film 10 and the substrate 11.

In order to obtain a relationship between the synthetic retardation $\Delta_{12}$ and the angle $\theta_{12}$ of the synthetic optical axis, the retardation $\Delta_1$ and the angle $\theta_1$ of the optical axis of the target thin film 10, and the retardation $\Delta_2$ and the angle $\theta_2$ of only the substrate 11 without the target thin film 10, a Jones matrix obtained by synthesizing the Jones matrices of the target thin film 10 and the substrate 11 is calculated.

Since the synthetic Jones matrix is the one obtained by multiplying the Jones matrix of the target thin film 10 and the Jones matrix of the substrate 11, the synthetic Jones matrix is represented by matrix (8-1) obtained by multiplying matrices (5) and (6). Matrix (8-1) is developed and rewritten to obtain matrix (8-2).

$$\begin{bmatrix} 1 - i\frac{\Delta_1}{2}\cos2\theta_1 & -i\frac{\Delta_1}{2}\sin2\theta_1 \\ -i\frac{\Delta_1}{2}\sin2\theta_1 & 1 + i\frac{\Delta_1}{2}\cos2\theta_1 \end{bmatrix} \begin{bmatrix} 1 - i\frac{\Delta_2}{2}\cos2\theta_2 & -i\frac{\Delta_2}{2}\sin2\theta_2 \\ -i\frac{\Delta_2}{2}\sin2\theta_2 & 1 + i\frac{\Delta_2}{2}\cos2\theta_2 \end{bmatrix} \quad (8\text{-}1)$$

$$\begin{bmatrix} 1 - i\frac{\Delta_1\cos2\theta_1 + \Delta_2\cos2\theta_2}{2} & -i\frac{\Delta_1\sin2\theta_1 + \Delta_2 + \sin2\theta_2}{2} \\ -i\frac{\Delta_1\sin2\theta_1 + \Delta_2\sin2\theta_2}{2} & 1 + \frac{\Delta_1\cos2\theta_1 + \Delta_2\cos2\theta_2}{2} \end{bmatrix} \quad (8\text{-}2)$$

Since matrices (8-2) and (7) are those for the optical element consisting of the substrate 11 and the thin film 10 and must be equal to each other.

Conditions for equalizing Jones matrix (8-2) with Jones matrix (7) are given by equations (9). That is, if equation (9) is established, the conditions for equation (8-2)=equation (7) are satisfied:

$$\begin{pmatrix} \Delta_{12}\cos2\theta_{12} = \Delta_1\cos2\theta_1 + \Delta_2\cos2\theta_2 \\ \Delta_{12}\sin2\theta_{12} = \Delta_1\sin2\theta_1 + \Delta_2\sin2\theta_2 \end{pmatrix} \quad (9)$$

The values measured by the optical system shown in FIG. 1 are the synthetic retardation $\Delta_{12}$ and the angle $\theta_{12}$ of the synthetic optical axis of the target thin film 10 and the substrate 11, and the retardation $\Delta_2$ and the angle $\theta_2$ of the optical axis of only the substrate 11. When these values, i.e., $\Delta_{12}$, $\theta_{12}$, $\Delta_2$, and $\theta_2$ are obtained, the retardation $\Delta_1$ and the angle $\theta_1$ of the optical axis of the target thin film 10 can be calculated in accordance with equations (10-1) and (10-2) obtained by solving equations (9) with respect to $\Delta_1$ and $\theta_1$:

$$\Delta_1 = \{\Delta_{12}^2 + \Delta_2^2 - 2\Delta_{12}\Delta_2\cos2(\theta_{12} - \theta_2)\}^{\frac{1}{2}} \quad (10\text{-}1)$$

$$\theta_1 = \frac{1}{2} \tan^{-1}\left( \frac{\Delta_{12} \sin 2\theta_{12} - \Delta_2 \sin 2\theta_2}{\Delta_{12} \cos 2\theta_{12} - \Delta_2 \cos 2\theta_2} \right) \quad (10\text{-}2)$$

The arithmetic operation circuit 34 in the arithmetic operation unit 30 shown in FIG. 1 performs arithmetic operations on the basis of equations (10-1) and (10-2) using the data $\Delta_{12}$, $\theta_{12}$, $\Delta_2$, and $\theta_2$, thereby calculating the values of the data $\Delta_1$ and $\theta_1$.

As described above, according to the above method of measuring the optical characteristics, the synthetic retardation $\Delta_{12}$ and the angle $\theta_{12}$ of the synthetic optical axis which are obtained by synthesizing the optical characteristics of both the target thin film 10 and the substrate 11 having the thin film 10 thereon, and the retardation $\Delta_2$ and the angle $\theta_2$ of the optical axis of only the substrate 11 are measured. The retardation $\Delta_1$ and the angle $\theta_1$ of the optical axis of the target thin film 10 are calculated by equations (10-1) and (10-2) in accordance with the synthetic retardation $\Delta_{12}$ and the angle $\theta_{12}$ of the synthetic optical axis and the retardation $\Delta_2$ and the angle $\theta_2$ of the optical axis of the substrate 11. The calculated optical characteristics, i.e., $\Delta_1$ and $\theta_1$, are the characteristics of only the target thin film 10 without including the optical characteristics of the substrate 11.

According to the above method of measuring the optical characteristics, the retardation $\Delta_1$ and the angle $\theta_1$ of the optical axis of the thin film 10 formed on the transparent substrate 11 can be accurately measured.

In the above embodiment, after the synthetic retardation $\Delta_{12}$ and the angle $\theta_{12}$ of the synthetic optical axis which are obtained by synthesizing the optical characteristics of both the target thin film 10 and the substrate 11 having the thin film 10 thereon are measured, the target thin film 10 is removed from the substrate 11, and the retardation $\Delta_2$ and the angle $\theta_2$ of the optical axis of the substrate 11 are measured. However, the retardation $\Delta_2$ and the angle $\theta_2$ of the optical axis of the substrate 11 may be measured before the synthetic retardation $\Delta_{12}$ and the angle $\theta_{12}$ of the synthetic optical axis are measured, i.e., before the target thin film 10 is formed on the substrate 11. The retardation $\Delta_{12}$ and the angle $\theta_{12}$ of the optical axis of the substrate 11 which are measured in advance are stored in the data holding circuit in the arithmetic operation unit 30. After the synthetic retardation $\Delta_{12}$ and the angle $\theta_{12}$ of the synthetic optical axis are measured, the stored data are output to the arithmetic operation circuit, and the optical characteristics of only the thin film 10 are calculated in accordance with the algorithm described above.

In this case, once the optical characteristics $\Delta_2$ and $\theta_2$ of substrates having the same quality are measured, optical characteristics of various thin films formed on the substrates having the same quality can be calculated using the measurement data $\Delta_2$ and $\theta_2$. Therefore, the retardation $\Delta_2$ and the angel $\theta_2$ of the optical axis of the substrate 11 need not be measured every time the optical characteristics of each thin film are to be measured.

Thermal and mechanical stresses may occur during formation of the thin film 10 depending on formation conditions of the thin film 10 to be formed on the substrate 11. If such stresses are likely to occur, preferably, the target thin film 10 is formed on the substrate 11, and the synthetic retardation $\Delta_{12}$ and the angle $\theta_{12}$ of the synthetic optical axis are measured. Thereafter, the target thin film 10 is removed, and the retardation $\Delta_2$ and the angle $\theta_2$ of the optical axis of the substrate 11 are measured.

In the above embodiment, the synthetic retardation $\Delta_{12}$ and the angle $\theta_{12}$ of the synthetic optical axis of the target thin film 10 and the substrate 11, and the retardation $\Delta_2$ and the angle $\theta_2$ of the optical axis of only the substrate 11 are measured using the optical system shown in FIG. 1. However, these measurements may be performed using an optical system having a $\lambda/4$ plate in place of the photoelastic modulator 3 in FIG. 1.

In this case, linearly polarized light passing through the polarizer 2 is converted into circularly polarized light by the $\lambda/4$ plate. When the analyzer 4 is rotated in the circumferential direction, the intensity of light detected by the photodetector 5 changes in accordance with the optical anisotropy of both the target thin film 10 and the substrate 11 or the optical anisotropy of only the substrate 11. The retardation and the angle of the optical axis of an optical element (i.e., a substrate having a thin film thereon, or only a substrate) located between the $\lambda/4$ plate and the analyzer 4 can be calculated on the basis of the change in light intensity.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method of measuring optical characteristics of a thin film formed on a transparent substrate, comprising:
    a first preparing step of preparing a transparent substrate;
    a second preparing step of preparing a thin film whose optical characteristics are to be measured and forming it on the transparent substrate;
    a first generating step of generating light and radiating the light on the thin film formed on the transparent substrate prepared in the second preparing step;
    a first detecting step of detecting a polarized state of light which is generated in the first generating step and has passed through the thin film and the transparent substrate;
    a synthetic retardation measuring step of measuring a value of a synthetic retardation and a direction of a synthetic optical axis of the transparent substrate and the thin film on the basis of the polarized state detected in the first detecting step;
    a second generating step of generating light and radiating the light on the transparent substrate prepared in the first preparing step;
    a second detecting step of detecting a polarized state of light which is generated in the second generating step and has passed through the transparent substrate;
    a substrate retardation measuring step of measuring a value of a synthetic retardation and a direction of a synthetic optical axis of only said transparent substrate on the basis of the polarized state detected in the second detecting step; and
    a retardation arithmetic operation step for calculating a value of a retardation and a direction of an optical axis of only said thin film on the basis of the value of the synthetic retardation and the direction of the synthetic optical axis which are measured in the synthetic retardation measuring step and the value of the retardation and the direction of the optical axis of only said transparent substrate, which are measured in the substrate retardation measuring step.

2. A method according to claim 1, wherein the retardation arithmetic operation step comprises an arithmetic operation step of measuring the value of the retardation and the direction of the optical axis of only said thin film on the basis of the following equations in accordance with the value of the synthetic retardation and the direction of the synthetic optical axis, and the value of the retardation and the direction of the optical axis of only said transparent substrate:

$$\Delta_1 = \{\Delta_{12}^2 + \Delta_2^2 - 2\Delta_{12}\Delta_2 \cos2(\theta_{12} - \theta_2)\}^{\frac{1}{2}}$$

$$\theta_1 = \frac{1}{2}\tan^{-1}\left(\frac{\Delta_{12}\sin2\theta_{12} - \Delta_2\sin2\theta_2}{\Delta_{12}\cos2\theta_{12} - \Delta_2\cos2\theta_2}\right).$$

$\Delta_1$: the retardation of said thin film
$\theta_1$: the angle of the optical axis of said thin film
$\Delta_2$: the retardation of said substrate
$\theta_2$: the angle of the optical axis of said substrate
$\Delta_{12}$: the synthetic retardation of said thin film and said substrate
$\theta_{12}$: the angle of the synthetic optical axis of said thin film and said substrate.

3. A method according to claim 1, wherein said synthetic retardation measuring step comprises a first substep of radiating light on said transparent substrate having said thin film thereon through a polarizer and a photoelastic modulator for continuously changing a polarized state of light transmitted through said polarizer, causing light emerging from said transparent substrate to be incident on a photodetector through an analyzer, and detecting a change in intensity of light transmitted through said analyzer, and a second substep of calculating the value of the synthetic retardation and the direction of the synthetic optical axis of said thin film and said transparent substrate on the basis of the change in intensity of light transmitted through said analyzer.

4. A method according to claim 1, wherein the substrate retardation measuring step is executed prior to the synthetic retardation measuring step.

5. A method according to claim 1, wherein the substrate retardation measuring step is executed after the synthetic retardation measuring step.

6. An apparatus for measuring optical characteristics of a thin film, comprising:
a light source for radiating light on a transparent substrate and on the transparent substrate having a thin film formed thereon, in a predetermined order;
a detector for detecting polarized states of lights which are generated by the light source and has passed through the transparent substrate, and through the thin film and the transparent substrate formed thereon, in said predetermined order;
a measuring circuit, connected to the detector, for measuring a retardation and a direction of an optical axis of a transparent substrate, and a synthetic retardation and a direction of a synthetic optical axis of said transparent substrate and said thin film formed thereon in said predetermined order, based on the polarized states detected by said detector;

a holding circuit, connected to the measuring circuit, for holding one of first data including the retardation and the direction of the optical axis of only said transparent substrate, which are measured by said measuring circuit, and second data including the synthetic retardation and the direction of the synthetic optical axis of said transparent substrate and said thin film formed thereon which are measured by said measuring circuit; and
retardation arithmetic operation means, connected to the holding circuit, for calculating a value of a retardation and a direction of an optical axis of only said thin film on the basis of said one data from said holding circuit and the other of said first and second data from said measuring circuit.

7. An apparatus according to claim 6, wherein said retardation arithmetic operating means comprises arithmetic operating means for calculating the value of the retardation and the direction of the optical axis of only said thin film on the basis of said one data of the first and second data from said holding means and the other data from said measuring means according to the following equations:

$$\Delta_1 = \{\Delta_{12}^2 + \Delta_2^2 - 2\Delta_{12}\Delta_2 \cos2(\theta_{12} - \theta_2)\}^{\frac{1}{2}}$$

$$\theta_1 = \frac{1}{2}\tan^{-1}\left(\frac{\Delta_{12}\sin2\theta_{12} - \Delta_2\sin2\theta_2}{\Delta_{12}\cos2\theta_{12} - \Delta_2\cos2\theta_2}\right).$$

$\Delta_1$: the retardation of said thin film
$\theta_1$: the angle of the optical axis of said thin film
$\Delta_2$: the retardation of said substrate
$\theta_2$: the angle of the optical axis of said substrate
$\Delta_{12}$: the synthetic retardation of said thin film and said substrate
$\theta_{12}$: the angle of the synthetic optical axis of said thin film and said substrate.

8. An apparatus according to claim 6, wherein said holding means stores the first data measured by said measuring means.

9. An apparatus according to claim 6, wherein said holding means stores the second data measured by said measuring means.

10. An apparatus according to claim 6, further comprising a control circuit, connected to said light source, detector, measuring means, and retardation arithmetic operation means, for controlling operations of said light source, detector, measuring means, and retardation arithmetic operation means.

11. A method of measuring optical characteristics of a thin film formed on a transparent substrate, comprising:
a first preparing step of locating a thin film whose optical characteristics are to be measured and which is formed on a transparent substrate between a polarizer and an analyzer;
a second preparing step of locating said transparent substrate without the film being formed thereon between the polarizer and the analyzer;
a first radiating step of radiating light through the polarizer onto the thin film formed on the transparent substrate prepared in the first preparing step;
a first detecting step of detecting a polarized state of light passed through the polarizer, the thin film, the transparent substrate and the analyzer;
a synthetic retardation measuring step of measuring a value of a synthetic retardation and a direction of a synthetic optical axis of the transparent substrate and the thin film formed thereon, on the basis of the polarized state detected in the first detecting step;

a second radiating step of radiating light through the polarizer onto the transparent substrate prepared in the second preparing step;

a second detecting step of detecting a polarized state of light passed through the polarizer, the transparent substrate, and the analyzer, a substrate retardation measuring step of measuring a value of a synthetic retardation and a direction of a synthetic optical axis of only said transparent substrate on the basis of the polarized state detected in the second detecting step; and a retardation arithmetic operation step for calculating a value of a retardation and a direction of an optical axis of only said thin film in accordance with the value of the synthetic retardation and the direction of the synthetic optical axis which are measured in the synthetic retardation measuring step and the value of the retardation and the direction of the optical axis of only said transparent substrate, which are measured in the substrate retardation measuring step.

12. A method according to claim 11, wherein the retardation arithmetic operation step comprises an arithmetic operation step of measuring the value of the retardation and the direction of the optical axis of only said thin film on the basis of the following equations in accordance with the value of the synthetic retardation and the direction of the synthetic optical axis, and the value of the retardation and the direction of the optical axis of only said transparent substrate:

$$\Delta_1 = \{\Delta_{12}^2 + \Delta_2^2 - 2\Delta_{12}\Delta_2 \cos 2(\theta_{12} - \theta_2)\}^{\frac{1}{2}}$$

$$\theta_1 = \frac{1}{2} \tan^{-1}\left(\frac{\Delta_{12} \sin 2\theta_{12} - \Delta_2 \sin 2\theta_2}{\Delta_{12} \cos 2\theta_{12} - \Delta_2 \cos 2\theta_2}\right).$$

$\Delta_1$: the retardation of said thin film
$\theta_1$: the angle of the optical axis of said thin film
$\Delta_2$: the retardation of said substrate
$\theta_2$: the angle of the optical axis of said substrate
$\Delta_{12}$: the synthetic retardation of said thin film and said substrate
$\theta_{12}$: the angle of the synthetic optical axis of said thin film and said substrate.

13. A method according to claim 11, wherein said synthetic retardation measuring step includes a step of changing a polarized state of light transmitted through said polarizer, by a photoelastic modulator.

14. An apparatus for measuring optical characteristics of a thin film, comprising:

a polarizer and an analyzer between which a sample, whose optical characteristics are to be measured, is located;

a photoelastic modulator, located between said polarizer and analyzer, for changing a polarized state of light transmitted through said polarizer;

a light source for radiating light on a transparent substrate, and on the transparent substrate on which a thin film is formed, through the polarizer and the photoelastic modulator, in a predetermined order;

detector means for detecting a polarized state of light which is generated by the light source and has passed through the polarizer, the photoelastic modulator, the transparent substrate, and the analyzer, and a polarized state of light which is generated by the light source and has passed through the polarizer, photoelastic modulator, the thin film and the transparent substrate, and the analyzer, in said predetermined order;

a measuring means, connected to the detector means, for measuring a retardation and a direction of an optical axis of the transparent substrate and a synthetic retardation and a direction of a synthetic optical axis of said transparent substrate having the thin film formed thereon, in a predetermined order, based on the polarized states detected by said detector means;

a holding means, connected to the measuring means, for holding one of the first data including the retardation and the direction of the optical axis of only said transparent substrate, which are measured by said measuring means, and second data including the synthetic retardation and the direction of the synthetic optical axis of said transparent substrate and said thin film, which are measured by said measuring means; and retardation arithmetic operation means, connected to the holding means, for calculating a value of a retardation and a direction of an optical axis of only said thin film on the basis of said one data from said holding means and the other data of said first and second data from said measuring means.

15. An apparatus according to claim 14, wherein said retardation arithmetic operating means comprises arithmetic operating means for calculating the value of the retardation and the direction of the optical axis of only said thin film on the basis of said one data of the first and second data from said holding means and the other data from said measuring means according to the following equations:

$$\Delta_1 = \{\Delta_{12}^2 + \Delta_2^2 - 2\Delta_{12}\Delta_2 \cos 2(\theta_{12} - \theta_2)\}^{\frac{1}{2}}$$

$$\theta_1 = \frac{1}{2} \tan^{-1}\left(\frac{\Delta_{12} \sin 2\theta_{12} - \Delta_2 \sin 2\theta_2}{\Delta_{12} \cos 2\theta_{12} - \Delta_2 \cos 2\theta_2}\right).$$

$\Delta_1$: the retardation of said thin film
$\theta_1$: the angle of the optical axis of said thin film
$\Delta_2$: the retardation of said substrate
$\theta_2$: the angle of the optical axis of said substrate
$\Delta_{12}$: the synthetic retardation of said thin film and said substrate
$\theta_{12}$: the angle of the synthetic optical axis of said thin film and said substrate.

16. An apparatus according to claim 14, wherein said holding means stores the first data measured by said measuring means.

17. An apparatus according to claim 14, wherein said holding means stores the second data measured by said measuring means.

* * * * *